United States Patent
Aouni et al.

(10) Patent No.: US 6,613,939 B2
(45) Date of Patent: Sep. 2, 2003

(54) PURIFIED SULFONATED ORGANOPHOSPHORUS COMPOUNDS AND CATALYSIS OF ORGANIC REACTIONS THEREWITH

(75) Inventors: Larbi Aouni, Bron (FR); Paolo Burattin, Lyons (FR); Pierre Coqueret, Francheville (FR); Marc Huser, Villeurbanne (FR)

(73) Assignee: Rhodia Fiber & Resin Intermediates, Courbevoie Cedex (FR)

( * ) Notice: Subject to any disclaimer, the term of this patent is extended or adjusted under 35 U.S.C. 154(b) by 0 days.

(21) Appl. No.: 09/887,043

(22) Filed: Jun. 25, 2001

(65) Prior Publication Data

US 2002/0016497 A1 Feb. 7, 2002

Related U.S. Application Data

(63) Continuation of application No. PCT/FR99/03234, filed on Dec. 21, 1999.

(30) Foreign Application Priority Data

Dec. 23, 1998 (FR) .............................................. 98/16586

(51) Int. Cl.$^7$ ............................................. C07C 309/32
(52) U.S. Cl. ......................................................... 562/35
(58) Field of Search ......................... 562/30, 35; 568/17

(56) References Cited

U.S. PATENT DOCUMENTS

| | | | | |
|---|---|---|---|---|
| 3,579,560 A | * | 5/1971 | Drinkard, Jr. et al. | |
| 4,248,802 A | * | 2/1981 | Kuntz | 568/454 |
| 4,623,490 A | | 11/1986 | Bexten et al. | |
| 4,668,824 A | | 5/1987 | Jenck et al. | |
| 5,684,182 A | * | 11/1997 | Naumann et al. | 562/35 |

OTHER PUBLICATIONS

CA:127:108740 abs of J Organomet Chem by Eckl et al 532(1–2) pp 243–249.*

* cited by examiner

*Primary Examiner*—Jean F Vollano
(74) *Attorney, Agent, or Firm*—Burns, Doane, Swecker & Mathis, L.L.P.

(57) ABSTRACT

Water-soluble sulfonated organophosphorus compounds are purified by at least partially removing contaminating sulfite values therefrom, by decreasing the pH of a solution of such sulfonated organophosphorus compounds to a value of less than or equal to 4, and maintaining the pH of the solution at this value of 4 or less for such period of time as to reduce the weight concentration of sulfite in the solution to less than 100 ppm; the organophosphorus compounds thus purified are well suited for the two-phase cocatalysis of a wide variety of organic reactions.

11 Claims, No Drawings

PURIFIED SULFONATED ORGANOPHOSPHORUS COMPOUNDS AND CATALYSIS OF ORGANIC REACTIONS THEREWITH

CROSS-REFERENCE TO PRIORITY/PCT APPLICATIONS

This application claims priority under 35 U.S.C. § 119 of FR-98/16586, filed Dec. 23, 1998, and is a continuation of PCT/FR99/03234, filed Dec. 21, 1999 and designating the United States (published in the French language on Jul. 6, 2000 as WO 00/39134; the title and abstract were also published in English), both hereby expressly incorporated by reference.

CROSS-REFERENCE TO COMPANION APPLICATIONS

Copending application Ser. No. 09/886,288 and Ser. No. 09/886,289, both filed Jun. 22, 2001, both assigned to the assignee hereof, and both also hereby expressly incorporated by reference.

BACKGROUND OF THE INVENTION

1. Technical Field of the Invention

The present invention relates to the preparation/purification of water-soluble sulfonated organophosphorus compounds which are particularly well suited as two-phase catalysts for a variety of organic reactions.

2. Description of the Prior Art

Organophosphorus compounds are particularly important as ligands for transition metal elements to prepare catalytic systems for various organic reactions such as carbonylation, hydroformylation, hydrocyanation and the isomerization of olefinic compounds.

Such catalytic systems are generally employed in reactions involving a single phase and, thus, an occasionally complex step of separation and recovery of the catalyst is required.

In the early 1970s, water-soluble compounds able to form complexes with metal elements in the oxidation state of zero were proposed as catalysts. These water-soluble compounds generally belong to the family of organophosphorus compounds comprising at least one sulfonate group. Thus, F. Joes and M. T. Beck, in an article published in *React. Kim. Catal. Letters*, 2, 257 (1975), and Bawoski et al., in an article published in the review *Nouv. J. Chem.*, 2, 137 (1978), describe a water-soluble monosulfonated triphenylphosphine which cannot be extracted using organic solvents.

The synthesis of these materials allowed the development of a novel method of catalysis referred to as two-phase catalysis. Specifically, the catalyst, i.e., transition metal elements complexed with water-soluble organophosphorus compounds, is present in an aqueous phase while the reagents are in an organic phase. Stirring and emulsification of the medium gives efficient catalysis. At the end of the reaction, the catalyst is recovered by simple separation by decantation of the two phases.

Rhône-Poulenc developed this technique for carrying out several important organic reactions such as the hydroformylation of olefins for the production of aldehydes, as described in FR-2,505,322 and FR-2,541,675. Another important application of this catalytic system, described, in particular, in FR-2,338,253 and FR-2,366,237, relates to the hydrocyanation reaction of olefins and the isomerization of the nitrites obtained, for example for the synthesis of adiponitrile, which is a major chemical intermediate for the manufacture of polyamide monomers.

Considerable research is nonetheless ongoing to improve the cost-effectiveness of these processes, in particular by increasing the cycle time and the lifetime of the catalytic system, as well as reducing the consumption of catalyst per quantity of adiponitrile produced.

Over the course of this research, degradation of the water-soluble sulfonated organophosphorus compounds has been observed.

SUMMARY OF THE INVENTION

Accordingly, a major object of the present invention is the provision of unique water-soluble sulfonated organophosphorus ligands which are resistant to degradation, and more stable two-phase catalytic systems comprised thereof.

Briefly, the present invention features carrying out organic reactions by two-phase catalysis, the media of reaction comprising an organic phase containing the reagents and the reaction products, an aqueous phase comprising a catalyst and a water-soluble sulfonated organophosphorus compound, wherein said water-soluble sulfonated organophosphorus compound has been purified via removal of contaminating sulfite compounds or radicals therefrom.

DETAILED DESCRIPTION OF BEST MODE AND SPECIFIC/PREFERRED EMBODIMENTS OF THE INVENTION

More particularly according to the present invention, in a preferred embodiment thereof, the sulfonated organophosphorus compounds thus purified have a weight concentration of sulfite of less than 100 ppm, preferably less than 50 ppm.

In another embodiment of this invention, the removal of sulfites is attained by converting same into sulfurous gas.

Exemplary organic reactions catalyzed via two-phase catalysis are hydroformylation, carbonylation, oxidation, isomerization and hydrocyanation reactions, in particular of unsaturated compounds.

In one preferred embodiment of the present invention, the hydrocyanation of organic compounds containing at least one ethylenic double bond is carried out to prepare nitrile compounds such as adiponitrile, for the synthesis of lactam, amino acid or amine monomers for the production of polyamides. This synthetic process, in particular, comprises a hydrocyanation of 3-pentenenitrile into adiponitrile, for which the catalyst comprising a sulfite-freed organophosphine in accordance with the invention as a component thereof is especially suitable.

Thus, in such an application, the lifetime of the catalyst can be greatly improved. This improvement is observed, in the case of the hydrocyanation of organic compounds comprising more than one ethylenic double bonds and in particular dienes, both for the hydrocyanation reaction of the first ethylenic bond and in that of the second ethylenic bond.

The process of the invention permits conducting the hydrocyanation of butadiene for the synthesis of adiponitrile with a catalyst based on water-soluble sulfonated organophosphorus ligands and on at least one metal element in oxidation state zero, with a consumption of catalyst per kg of adiponitrile produced which is markedly lower than that existing when using a catalyst or a ligand which has not been subjected to removal of sulfites.

In another preferred embodiment of the invention, removal of the sulfites contained in the water-soluble sulfonated organophosphorus compound is obtained by lowering the pH of the solution of organophosphorus compounds to a value of less than or equal to 4 and maintenance of such solution at a pH of less than or equal to 4 until a sulfite concentration in the solution of less than 100 ppm is attained.

Assay of the sulfite compounds in the solution is carried out, for example, by ionic chromatography.

The lowering of the pH of the solution can be accomplished by any suitable means. However, in another preferred embodiment of the invention, this lowering is accomplished by addition of a strong inorganic or organic acid in pure form or, more preferably, in solution.

The acidic solution can be a concentrated or dilute solution.

Exemplary acids which are suitable according to the present invention, representative are those acids having, for example, a pKa of less than or equal to 4, the corresponding anhydrides and more generally any compound which is chemically inert with respect to the organophosphorus compound and which can lower the pH of a solution.

Exemplary such acids are sulfuric acid, hydrochloric acid, trifluoroacetic acid, para-toluenesulfonic acid, perchloric acid and nitric acid.

Moreover, the solution of water-soluble sulfonated organophosphorus compounds is preferably an aqueous solution. However, solutions using water/alcohol mixtures as solvent are also suitable. The alcohol can be replaced with any water-miscible solvent.

In another embodiment of the invention, the solution is maintained at a pH of less than or equal to 4, at a temperature below 100° C. and advantageously ranging from 40° C. to 90° C.

The sulfurous gas produced by converting the sulfites is, in one preferred embodiment of the invention, removed from the reaction medium by entrainment with a carrier fluid. This carrier fluid is preferably nonoxidizing. Thus, carrier fluids which are suitable for the invention are, for example, nitrogen, carbon dioxide, water vapor, rare or inert gases, and oxygen-depleted air.

The water-soluble sulfonated organophosphorus compounds which are suitable for treatment according to the process of the invention and which are useful as ligands in the processes of two-phase catalysis are generally the sulfonated organophosphorus compounds prepared via one or more sulfonation steps as described in the article published in *J. Chem. Soc.*, pages 276–288 (1958) or in GB-1,066,261. These can also be prepared by reacting sodium p-chlorobenzenesulfonate with diphenylchlorophosphine, as described in the article by H. Schindlbauer, *Monatsch. Chem.*, 96, pages 2051–2057 (1965).

Generally, these processes for synthesizing sulfonated organophosphorus compounds do not make it possible to obtain a compound which is free of sulfite compounds or radicals. Consequently, in order to avoid degradation of these compounds during their use as a catalyst or a ligand of a catalytic system, it is necessary according to the process of the invention to remove these sulfites at least partially.

Suitable water-soluble sulfonated phosphine compounds according to the invention include those described in FR-2, 338,253 or in WO 97/12857 and EP 0,650,959.

Thus, suitable phosphines according to this invention have the following structural formula (I):

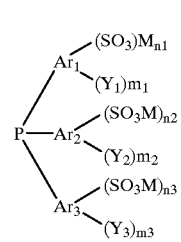

(I)

in which $Ar_1$, $Ar_2$ and $Ar_3$, which may be identical or different, are each an aryl radical; $Y_1$, $Y_2$ and $Y_3$, which may be identical or different, are each an alkyl radical having from 1 to 4 carbon atoms, an alkoxy radical having from 1 to 4 carbon atoms, a halogen atom, a CN group, an $NO_2$ group, an OH group, an $NR_1R_2$ radical, wherein $R_1$ and $R_2$, which may be identical or different, are each an alkyl radical having from 1 to 4 carbon atoms; M is an inorganic or organic cationic residue selected, such that the compound of formula (I) is soluble in water, from the group consisting of $H^+$, cations derived from alkali metals or alkaline earth metals, $N(R_3R_4R_5R_6)^+$, wherein $R_3$, $R_4$, $R_5$ and $R_6$, which may be identical or different, are each an alkyl radical having from 1 to 4 carbon atoms or a hydrogen atom, and other metal cations, the benzenesulfonic acid salts of which are soluble in water; $m_1$, $m_2$ and $m_3$ which may be identical or different, are each an integer ranging from 0 to 5; and $n_1$, $n_2$ and $n_3$, which may be identical or different, are each an integer ranging from 0 to 3, at least one of these being equal to or greater than 1.

Exemplary metals, the benzenesulfonic acid salts of which are soluble in water, include lead, zinc and tin.

By the expression "soluble in water" is generally intended a compound soluble to at least 0.01 g per liter of water.

Preferred phosphines of formula (I) are those in which:
$Ar_1$, $Ar_2$ and $Ar_3$ are phenyl radicals;
$Y_1$, $Y_2$ and $Y_3$ are alkyl radicals having from 1 to 2 carbon atoms, or alkoxy radicals having from 1 to 2 carbon atoms;
M is a cation selected from the group consisting of $H^+$, cations derived from Na, K, Ca and Ba, $NH_4^+$, and tetramethylammonium, tetraethylammonium, tetrapropylammonium and tetrabutylammonium cations;
$m_1$, $m_2$ and $m_3$ are integers ranging from 0 to 3; and
$n_1$, $n_2$ and $n_3$ are integers ranging from 0 to 3, at least one also being greater than 1.

The more particularly preferred phosphines are the sodium, potassium, calcium, barium, ammonium, tetramethylammonium and tetraethylammonium salts of mono(sulfophenyl)diphenylphosphine, di(sulfophenyl) phenylphosphine and tri(sulfophenyl)phosphine, in which the $SO_3$ groups are preferably in the meta-position.

Exemplary phosphines of formula (I) according to the process of the invention are alkali metal or alkaline earth metal salts, ammonium salts, or quaternary ammonium salts of (3-sulfo-4-methylphenyl)di(4-methylphenyl)phosphine, (3-sulfo-4-methoxyphenyl)di(4-methoxyphenyl)phosphine, (3-sulfo-4-chlorophenyl)di(4-chlorophenyl)phosphine, di(3-sulfophenyl)phenylphosphine, di(4-sulfophenyl) phenylphosphine, di(3-sulfo-4-methylphenyl)(4-methylphenyl)phosphine, di(3-sulfo-4-methoxyphenyl)(4-methoxyphenyl)phosphine, di(3-sulfo-4-chlorophenyl)(4-chlorophenyl)phosphine, tri(3-sulfophenyl)phosphine, tri(4-sulfophenyl)phosphine, tri(3-sulfo-4-methylphenyl) phosphine, tri(3-sulfo-4-methoxyphenyl)phosphine, tri(3- sulfo-4-chlorophenyl)phosphine, (2-sulfo-4-methylphenyl)
(3-sulfo-4-methylphenyl)(3,5-disulfo-4-methylphenyl)
phosphine or (3-sulfophenyl)(3-sulfo-4-chlorophenyl)(3,5-disulfo-4-chlorophenyl)phosphine.

A mixture of these phosphines can of course be employed, in particular a mixture of mono-, di- and tri-meta-sulfonated phosphines.

Monodentate and bidentate phosphines having the following structural formulae (II) and (III) are also suitable according to the present invention:

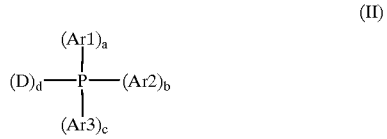

(II)

in which Ar1 and Ar2, which may be identical or different, are each aryl radicals or substituted such aryl radicals bearing one or more substituents, such as alkyl or alkoxy radicals having from 1 to 4 carbon atoms, halogen atoms, hydrophilic groups, such as —COOM, —SO$_3$M or —PO$_3$M, wherein M is an inorganic or organic cationic residue selected from among hydrogen, cations derived from alkali metals or alkaline earth metals, ammonium cations —N(R)$_4$, wherein the radicals R, which may be identical or different, are each a hydrogen atom or an alkyl radical having from 1 to 4 carbon atoms, and other cations derived from metals, the arylcarboxylic acid, arylsulfonic acid or arylphosphonic acid salts of which are soluble in water, —N(R)$_4$, wherein the radicals R, which may be identical or different, are each a hydrogen atom or an alkyl radical having from 1 to 4 carbon atoms, or —OH; Ar$_3$ is a substituted aryl radical bearing one or more substituents, such as alkyl or alkoxy radicals having from 1 to 4 carbon atoms, halogen atoms, hydrophilic groups, such as —COOM or —PO$_3$M, wherein M is an inorganic or organic cationic residue selected from among hydrogen, cations derived from alkali metals or alkaline earth metals, ammonium cations —N(R)$_4$, wherein the radicals R, which may be identical or different, are each a hydrogen atom or an alkyl radical having from 1 to 4 carbon atoms, and other metal cations, the arylcarboxylic acid or arylphosphonic acid salts of which are soluble in water, N(R)$_4$, wherein the radicals R, which may be identical or different, are each a hydrogen atom or an alkyl radical having from 1 to 4 carbon atoms, or —OH, with the proviso that at least one of the substituents of Ar$_3$ is a hydrophilic group as defined above; a is 0 or 1; b is 0 or 1; c is an integer ranging from 0 to 3; D is an alkyl radical, a cycloalkyl radical or an alkyl or cycloalkyl radical substituted by one or more substituents, such as an alkoxy radical having from 1 to 4 carbon atoms, a halogen atom, a hydrophilic group, such as —COOM, —SO$_3$M or —PO$_3$M, wherein M is an inorganic or organic cationic residue selected from among hydrogen, cations derived from alkali metals or alkaline earth metals, ammonium cations —N(R)$_4$, wherein the radicals R, which may be identical or different, are each a hydrogen atom or an alkyl radical having from 1 to 4 carbon atoms, and other metal cations, the arylcarboxylic acid, arylsulfonic acid or arylphosphonic acid salts of which are soluble in water, —N(R)$_4$, wherein the radicals R, which may be identical or different, are each a hydrogen atom or an alkyl radical having from 1 to 4 carbon atoms, or —OH; d is an integer ranging from 0 to 3; and the sum (a+b+c+d) is equal to 3; and

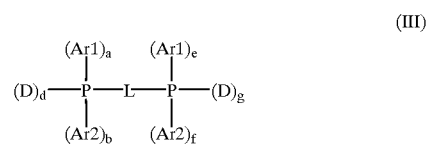

(III)

in which Ar1, Ar2 and D are as defined above for the formula (II); a, b, e, and f are each 0 or 1; d and g are each an integer ranging from 0 to 2; the sum (a+b+d) is equal to 2; the sum (e+f+g) is equal to 2; and L is a single valency bond or a divalent hydrocarbonaceous radical, such as an alkylene radical, a cycloalkylene radical, an arylene radical, or a radical deriving from a heterocycle comprising one or two oxygen, nitrogen or sulfur atoms in the ring, these various cyclic radicals being bonded directly to one of the phosphorus atoms or both phosphorus atoms or being bonded to one of the phosphorus atoms or to both via a linear or branched alkylene radical having from 1 to 4 carbon atoms, with the proviso that the ring or rings which are optionally moieties of the divalent radical L may comprise one or more substituents, such as an alkyl radical having from 1 to 4 carbon atoms.

Exemplary phosphines of structural formula (II) include tris(hydroxymethyl)phosphine, tris(2-hydroxyethyl) phosphine, tris(3-hydroxypropyl)phosphine, tris(2-carboxymethyl)phosphine, the sodium salt of tris(3-carboxyphenyl)phosphine, tris(3-carboxyethyl)phosphine, tris(4-trimethylammoniophenyl)phosphine iodide, the sodium salt of tris(2-phosphonoethyl)phosphine or bis(2-carboxyethyl)phenylphosphine.

And exemplary phosphines of structural formula (III) include the sodium salt of 2,2'-bis[di(sulfophenyl) phosphino]-1, 1'-binaphthyl, the sodium salt of 1,2-bis[di (sulfophenyl)phosphinomethyl]cyclobutane (CBDTS), 1,2-bis(dihydroxymethylphosphino)ethane, 1,3-bis (dihydroxymethylphosphino)propane, or the sodium salt of 2,2'-bis[di(sulfophenyl)phosphinomethyl] -1,1'-binaphthyl.

Certain of the water-soluble phosphines of formulae (I) to (III) are commercially available.

For the preparation of the others, reference is made to the general or specific processes for the synthesis of phosphines described in the general literature, such as Houben-Weyl, *Methoden der organischen Chemie*, "organische Phosphor Verbindungen" [*Methods of Organic Chemistry*, "Organic Phosphorus Compounds"], Part 1(1963).

Lastly, for the preparation of water-soluble derivatives which have not been described, starting from phosphines not comprising water-soluble substituents described above, one or more of these hydrophilic substituents are introduced. Thus, sulfonate groups, for example, may be introduced by the reaction of SO$_3$ in sulfuric acid. Carboxylate, phosphonate and quaternary ammonium groups can likewise be introduced via the usual chemical techniques for this type of synthesis.

Other water-soluble sulfonated organophosphorus compounds which are suitable are the compounds BISBIS, NORBOS and BINAS described in the article by Boy Cornils and Emile G. Kuntz, published in *Journal of Organometallic Chemistry*, No. 502 (1995) pp. 177–186. Also suitable are the water-soluble furylphosphine compounds described in French patent application No. 98/06559, filed May 20, 1998, assigned to the assignee hereof.

As indicated above, the subject sulfite-freed organophosphorus compounds are particularly useful as components of catalysts comprising a transition metal element selected, for example, from the group consisting of nickel, cobalt, iron, ruthenium, rhodium, palladium, osmium, iridium, platinum, copper, silver, gold, zinc, cadmium and mercury in variable oxidation states.

It should be appreciated that, in these catalysts, generally, rhodium is in oxidation state (I), ruthenium is in oxidation state (II), platinum is in oxidation state (I), palladium is in oxidation state (II), osmium is in oxidation state (0), iridium is in oxidation state (0) and nickel is in oxidation state (0).

In order to further illustrate the present invention and the advantages thereof, the following specific examples are given, it being understood that same are intended only as illustrative and in nowise limitative.

EXAMPLE 1

19.2 kg of an aqueous solution containing 30% by weight of the sodium salt of triphenylphosphine trisulfonate and initially containing 1,540 ppm of sulfites (pH=6.2) were introduced into a 20 liter reactor stirred with a turbomixer (180 rpm) and fitted with an ascending condenser, a nitrogen inlet via a dipping cannula and a bubbler containing an aqueous sodium hydroxide solution (1 mol/liter). This solution was degassed. 222 g of an aqueous sulfuric acid solution at 2 mol/liter were then introduced, which provided a pH of 1.8. This mixture was heated to 80° C. with stirring and under a stream of nitrogen such as to entrain the sulfurous gas. Assay of the sulfites by ionic chromatography on samples withdrawn every 15 minutes made it possible to monitor the conversion of the sulfites into sulfur dioxide. After 1 hour at 80° C., the assay in question gave the following result: 80 ppm of sulfites. After 1 h, 45 minutes, the sulfite content became less than or equal to 40 ppm (detection limit of the ionic chromatography analysis). After 2 hours at 80° C., the mixture was cooled with stirring to room temperature. 324 g of an aqueous sodium hydroxide solution at 1 mol/liter were then introduced and a sulfite-freed aqueous solution of TPPTS (pH=5.4) was obtained.

EXAMPLE 2

500 cm³ of the sulfite-freed aqueous solution of TPPTS at 30% by weight, of Example 1, were introduced into a 1 liter glass round-bottomed flask fitted with a magnetic stirring bar and an ascending condenser. The solution was degassed. 20 g of Ni (cyclooctadiene)₂ were then introduced, with stirring and under a stream of nitrogen, followed by 350 cm³ of pre-degassed orthoxylene. This mixture was heated at 45° C. for 15 h. After cooling, the two-phase system was decanted. About 35 cm³ of the aqueous phase, which had a deep red coloration, were withdrawn and introduced into a 150 cm³ glass reactor fitted with a turbomixer and purged with argon. This aqueous phase was heated to 90° C. and 3.2 cm³ of an aqueous solution of zinc chloride at 70% by weight were then added. The mixture was maintained at 90° C. with stirring for 48 hours. After cooling to room temperature, a sample of the aqueous solution was withdrawn and analysed by phosphorus-31 NMR (nuclear magnetic resonance). The analysis, performed on a Bruker AMX 300 II® spectrometer at a frequency of 121 MHZ, evidenced that the TPPTS contained no TPPTS sulfide (content less than the detection limit of the analysis technique, i.e., less than 0.1 mol % of the total phosphorus in solution).

EXAMPLE 3

500 cm³ of the aqueous solution of TPPTS at 30% by weight, initially containing 1,540 ppm of sulfites, were introduced into a 1 liter glass round-bottomed flask fitted with a magnetic stirring bar and an ascending condenser. The solution was degassed. 20 g of Ni(cyclooctadiene)₂ were then introduced, with stirring and under a stream of argon, followed by 350 cm³ of pre-degassed ortho-xylene. This mixture was heated at 45° C. for 15 h. After cooling, the two-phase system was decanted. About 35 cm³ of the aqueous phase, which had a deep red coloration, were withdrawn and introduced into a 150 cm³ glass reactor fitted with a turbomixer and purged with argon. This aqueous phase was heated to 90° C. and 3.2 cm³ of an aqueous solution of zinc chloride at 70% by weight were then added. The mixture was maintained at 90° C. with stirring at 48 hours. After cooling to room temperature, a sample of the aqueous solution was withdrawn and analysed by phosphorus-31 NMR (nuclear magnetic resonance). The analysis in question, performed on a Bruker AMX 300 II spectrometer at a frequency of 121 MHZ, evidence that it contained TPPTS sulfide (peak at 43.7 ppm) to an extent of 4.5 mol % of the total phosphorus in solution.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the purification of water-soluble sulfonated organophosphine compounds by at least partially removing contaminating sulfites therefrom, comprising decreasing the pH of a solution of said sulfonated organophosphine compounds to a value of less than or equal to 4, converting the sulfites into a sulfurous oxide gas and removing said gas from said solution, and maintaining the pH of said solution at this value of 4 or less for such period of time as to reduce the weight concentration of sulfite in said solution to less than 100 ppm.

2. The process as defined by claim 1, comprising maintaining the pH of said solution at the value of 4 or less for such period of time as to reduce the weight concentration of sulfite in said solution to less than 50 ppm.

3. The process as defined by claim 1, comprising decreasing the pH of said solution by adding an acidic compound thereto.

4. The process as defined by claim 3, said acidic compound comprising a strong inorganic or organic acid.

5. The process as defined by claim 4, said strong acid having a pKa of 4 or less.

6. The process as defined by claim 5, said strong acid being selected from the group consisting of sulfuric acid, hydrochloric acid, trifluoroacetic acid, para-toluenesulfonic acid, perchloric acid and nitric acid.

7. The process as defined by claim 1, comprising maintaining the temperature of said solution at less than 100° C.

8. The process as defined by claim 7, comprising maintaining the temperature of said solution at a value ranging from 40° C. to 90° C.

9. The process as defined by claim 1, comprising removing said sulfurous oxide gas from said solution by entraining same in a carrier fluid.

10. The process as defined by claim 9, said carrier fluid comprising nitrogen, carbon dioxide, water vapor, a rare or inert gas, or an oxygen-depleted air.

11. The process as defined by claim 1, wherein said solution of sulfonated organophosphine compound comprising an aqueous or water/alcohol solution.

* * * * *